United States Patent [19]
Thompson et al.

[11] Patent Number: 5,289,723
[45] Date of Patent: Mar. 1, 1994

[54] ANTISYMMETRIC GRAIN SUPPORT TEST DEVICE AND METHODS

[75] Inventors: James R. Thompson, Boaz, Ala.; John M. Nelson, Tomio Sato, Toby T. Norris, all of Huntsville, Ala.

[73] Assignee: Thiokol Corporation, Ogden, Utah

[21] Appl. No.: 893,721

[22] Filed: Jun. 5, 1992

[51] Int. Cl.$^5$ .............................................. G01N 3/24
[52] U.S. Cl. ........................................ 73/842; 73/846
[58] Field of Search ............... 73/818, 819, 821, 827, 73/831, 833, 834, 837, 841, 842, 845, 846, 856, 859, 860, 865.8, 865.6

[56] References Cited

U.S. PATENT DOCUMENTS

| | | | |
|---|---|---|---|
| 2,702,929 | 3/1955 | Ladden et al. | 73/859 |
| 3,224,259 | 12/1965 | De Nicola | 73/859 |
| 3,745,051 | 7/1973 | Griffin et al. | 73/827 |
| 4,483,198 | 11/1984 | Smith et al. | 73/794 |
| 4,523,475 | 6/1985 | Bills, Jr. et al. | 73/781 |

FOREIGN PATENT DOCUMENTS

| | | | |
|---|---|---|---|
| 276483 | 10/1970 | U.S.S.R. | 73/842 |
| 1359711 | 12/1987 | U.S.S.R. | 73/841 |
| 1629807 | 2/1991 | U.S.S.R. | 73/827 |

*Primary Examiner*—Robert Raevis
*Attorney, Agent, or Firm*—Madson & Metcalf

[57] ABSTRACT

A testing apparatus and methods for use with a tensile testing machine for simulating thermal, acceleration, and ignition pressurization loads upon a grain support system of a solid rocket motor during ignition. The apparatus includes a pair of antisymmetrically disposed L-shaped test fixtures within which is attached a test specimen. The test specimen is configured to simulate two propellant grain support systems. The grain support systems in the test specimen are antisymmetrically disposed, thereby permitting two specimens to be tested simultaneously by the application of uniaxial tension to the apparatus.

19 Claims, 3 Drawing Sheets

ANTISYMMETRIC GRAIN SUPPORT TEST DEVICE AND METHODS

BACKGROUND

1. The Field of the Invention

The present invention is related to an apparatus and methods for simulating thermal, acceleration, and ignition pressurization loads upon the grain support system of a solid rocket motor during ignition. More particularly, the present invention is related to an antisymmetric test device for use in applying uniaxial tension on an antisymmetric test specimen designed to simulate the grain support system of a solid rocket motor.

2. Technical Background

A typical solid rocket motor essentially consists of a steel casing filled with a solid propellant grain. A grain support system is utilized to affix the grain within the casing. A typical grain support system consists of a layer of insulation bonded between the propellant grain and the casing. The layer of insulation provides a surface to which the propellant grain may be bonded and assists in shielding the casing from the extreme heat generated when the propellant is ignited.

In the manufacture of the solid rocket motor, the layer of insulation is generally bonded to the rocket casing (or to a liner which in turn is bonded to the casing) through a vulcanization process. That is, the insulation is laid up in the case in a "green" state. As it cures, it bonds to the casing. The grain is then cast onto the insulation with the use of a mold to form an initial internal configuration in the propellant grain.

It will be appreciated that maintaining the integrity of the bonds between the insulation and the casing, and between the insulation and the propellant grain, during ignition of the solid rocket motor is critical to the success of the motor.

When a solid rocket motor is ignited, the bonds within the motor are subjected to extreme forces from a variety of sources. As the rocket accelerates, acceleration loads act upon the bonds. During acceleration, the thrust created by the burning propellant acts upon the head end of the motor. Thus, the grain support system holding the propellant within the motor must be sufficiently strong to prevent the unburned propellant from breaking away and falling out of the motor during acceleration. Of greater practical concern, however, the grain support system must also be sufficiently strong to prevent any significant deformation in the grain, as deformation in the propellant grain can adversely impact the firing characteristics of the motor.

Among the other loads acting on the grain support system are ignition pressurization loads. Ignition pressurization loads tend to expand the case, causing the case to move away from the propellant. In response to these and other loads which induce stress in the propellant grain, and generally tend to separate the propellant from the case, stress relief flaps have been incorporated into some solid rocket motors.

Stress-relief flaps essentially comprise a hinge near the head end of the motor between the case and the layer of insulation surrounding the propellant. Thus, when the forces tending to separate the insulation and propellant from the case are sufficiently strong, the flap will open by permitting pivoting about the hinge, thereby permitting limited separation of the case and the insulation while preserving the integrity of the bonds.

Stress-relief flaps are typically constructed of a moldable material having some insulating value. Such materials include Kevlar and polyisoprene. The flaps may be reinforced with long fibers extending along the entire length of the flap to prevent the flap from tearing. These stress-relief flaps are typically designed such that when they open, they do not induce high strains in the propellant at or near the base of the flap. The use of an appropriately designed flap can also reduce the amount of insulation required at the base of the flap, thereby permitting the use of more propellant and improving performance of the motor.

Thermal loads resulting from the unequal thermal expansion of the case and the propellant during ignition load the stress-relief flap in a manner similar to ignition pressurization loads. In a typical solid rocket motor, the thermal expansion of the propellant may be ten times the expansion of the case. By providing a stress-relief flap, a measured degree of separation of the grain and the case is permitted and the stress to the bonds and the remainder of the grain support system due to the thermal loads is relieved.

As can be appreciated from the foregoing, the continued improvement in the design of solid rocket motors requires testing and analysis to develop grain support systems which include improved bonds and which utilize bond reinforcement devices, such as stress-relief flaps, to increase the effective strength of the bonds. One of the principal methods of testing grain support systems is to test fire a solid rocket motor incorporating the system to be tested. Data obtained from the test can be utilized in determining how well the grain support system will perform under actual launch conditions.

One of the principal disadvantages of this testing method is its expense. For example, if it is desired to test propellant grain reinforcement systems in the solid rocket motors used on the space shuttle, the extreme expense in test firing such motors merely to test a wide variety of experimental designs obviously renders such an approach unfeasible.

Also, the nature of the data which can be obtained from such a test is limited. During a test firing it is difficult to monitor the exact load at which the bonds begin to fail. Such monitoring would be accomplished most effectively by visually monitoring the grain support system as the loads are applied. Obviously, this is not possible during the ignition of a rocket motor, even if the test is a static firing of the motor.

In response to the difficulties and expense of testing grain support systems through firing experimental rocket motors, other testing methods have been developed. One method which continues to be used extensively is finite element analysis. In this method, the reaction of bonds and bond-reinforcement devices to stresses are analytically predicted. A primary advantage to the use of finite element analysis is its low cost, as compared with physical testing through firing of the motor.

The use of finite element analysis, however, is limited in its ability to accurately predict the reaction of experimental materials. Finite element analysis is best suited for use when the physical properties of the materials being employed are well known. In the development of solid rocket motors, however, much of the experimental work is focused on employing materials whose physical properties vary. These materials include composite materials utilizing variations of fiber reinforcement. Such materials are not well suited to analysis using finite element methods.

Thus, it would be an advancement in the art to provide an apparatus and method for testing propellant grain support systems which can be effectively utilized to test materials about which physical properties may not be known.

It would be an additional advancement in the art to provide such an apparatus and method which could be used in the testing of propellant grain support systems which could provide a physical test without the extreme cost attendant in preparing a solid rocket motor according to the experimental design and firing the motor.

It would be a further advancement in the art if such an apparatus and method could be provided to test propellant grain support systems whereby bonds and bond reinforcement systems, such as stress-relief flaps, could be visually monitored during the test, thereby obtaining specific data on the location of debonding and deformation.

Such an apparatus and method are disclosed and claimed herein.

BRIEF SUMMARY AND OBJECTS OF THE INVENTION

The present invention is directed to a novel apparatus and methods for use with a tensile testing machine whereby thermal, acceleration, and ignition pressurization loads upon the grain support system of a solid rocket motor during ignition may be simulated. The apparatus includes a test specimen which is prepared with an antisymmetric configuration. For purposes of this application, the term "antisymmetric" indicates a correspondence of size, shape and relative position with respect to two parts such that lines connecting corresponding points on the two parts intersect at substantially a single point or axis. Each specimen includes two antisymmetrically disposed grain support systems, including a portion of propellant grain. The test specimen is prepared by bonding it to the side segments of two L-shaped test fixtures including means for attachment to a tensile testing machine.

In one embodiment, a mold is provided within which a pair of steel, L-shaped steel test fixtures are placed. The test fixtures are positioned within the mold in an antisymmetric configuration with respect to each other. The test specimen is then prepared within the void located between the test fixtures.

The test specimen is prepared by configuring each side of the specimen to correspond to the grain support system desired to be tested. One example of such a specimen is prepared by initially bonding a stress-relief flap along the side elements of each of the test fixtures. A layer of insulation is then laid up against the stress-relief flap and along the remaining exposed side of the test fixtures to form the sides of the test specimen. The insulation is bonded into place by a vulcanization process. Finally, a propellant grain is cast into the mold to fill the void left between the layers of insulation.

The testing device, consisting of the test fixtures and the antisymmetric grain support system, can then be removed from the mold and placed in a tensile testing machine for testing. By utilizing a tensile testing machine, the forces which arise because of acceleration, ignition pressurization, and thermal expansion during ignition of a solid rocket motor can be duplicated, and their impact on the grain support system can be evaluated.

The device enables two test samples of the grain support system to be tested simultaneously. The antisymmetric nature of the testing device prevents the action of one grain reinforcing system from effecting the action of the other. Thus, as the device is placed under a load, the reactions of the two grain support systems are independent, enabling two sets of data to be collected for each test conducted. Because the test specimen is prepared to duplicate the cross-section of the grain support system to be tested, specific data can be obtained concerning the effectiveness of stress-relief flaps and the bonds within the grain support system. Advantageously, the test specimen can be visually monitored during testing to ascertain information which could not be obtain during actual ignition of a motor.

Thus, it is an object of the present invention to provide apparatus and methods for testing propellant grain support systems which can be effectively utilized to test materials and bonding methods about which physical properties may not be known.

It is an additional object of the present invention to provide such apparatus and methods which may be used in the testing of propellant grain support systems to provide a physical test without the extreme cost attendant in preparing a solid rocket motor according to the experimental design and firing the motor.

It is a further object of the present invention to provide such apparatus and methods for testing propellant grain support systems whereby bonds and bond reinforcement systems, such as stress-relief flaps, can be visually monitored during the test, thereby providing specific data on the location of debonding and deformation.

These and other objects and advantages of the present invention will become more fully apparent by examination of the following description of the preferred embodiments and the accompanying drawings.

DETAILED DESCRIPTION OF THE PREFERRED EMBODIMENTS

Figure 1:
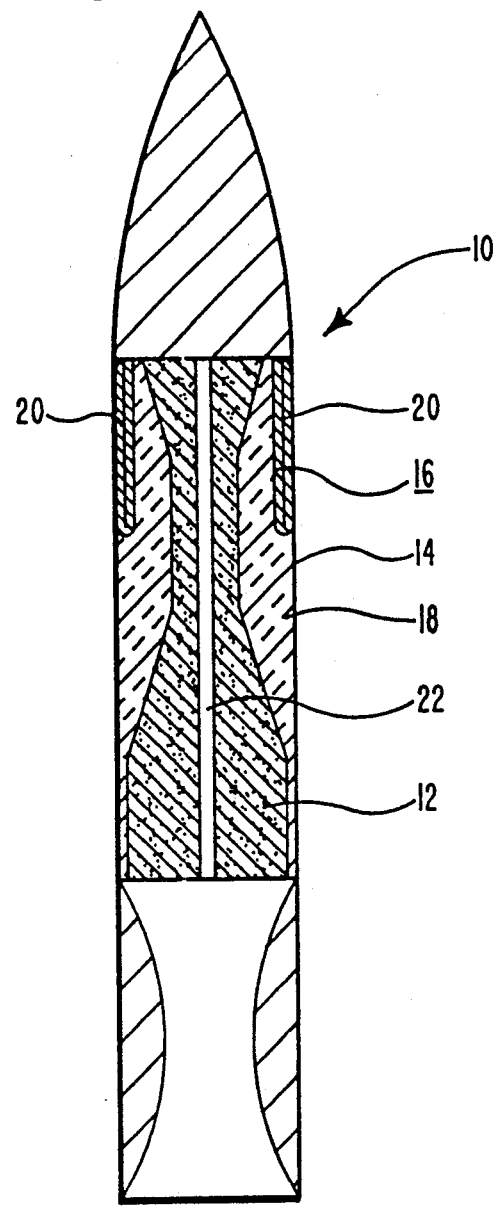
FIG. 1 is a cross-sectional view of a solid rocket motor employing a grain support device which includes stress-relief flaps.

Reference is now made to the FIGURES wherein like parts are referred to by like numerals throughout. With particular reference to FIG. 1, a typical solid rocket motor is illustrated at 10. The solid rocket motor 10 includes propellant grain 12, a steel casing 14 and a grain support system 16.

With continued reference to FIG. 1, the support system 16 may include a layer of insulation 18 and a stress-relief flap 20. Is it also typical for a solid rocket motor to include a liner between the casing 14 and the insulation 18. A core 22 is configured within the propellant grain 12 and is formed with an initial internal configuration according to the burn characteristics desired in the rocket motor.

During ignition of the rocket 10, the three principal loads acting upon the propellant grain are acceleration loads, ignition pressurization loads and thermal loads. These loads tend to force the propellant grain 12 to separate from the grain support 16. The inclusion of a stress-relief flap 20 in the support is one mechanism utilized to prevent uncontrolled deformation of the propellant grain 12. If the deformation in the propellant grain occurring during ignition of the rocket motor can be controlled or predicted, the internal configuration of the propellant grain may be altered to compensate for the deformation.

Hence, it is important that the grain support system be designed such that it will not only prevent failure of the bond holding the propellant grain inside the motor, but such that any deformation in the grain can be predicted. By utilizing the present invention, a variety of grain support systems may be easily and efficiently tested, thereby enabling the generation of data concerning the strength of various grain support systems and any deformation to be expected under given loads.

Figure 2:
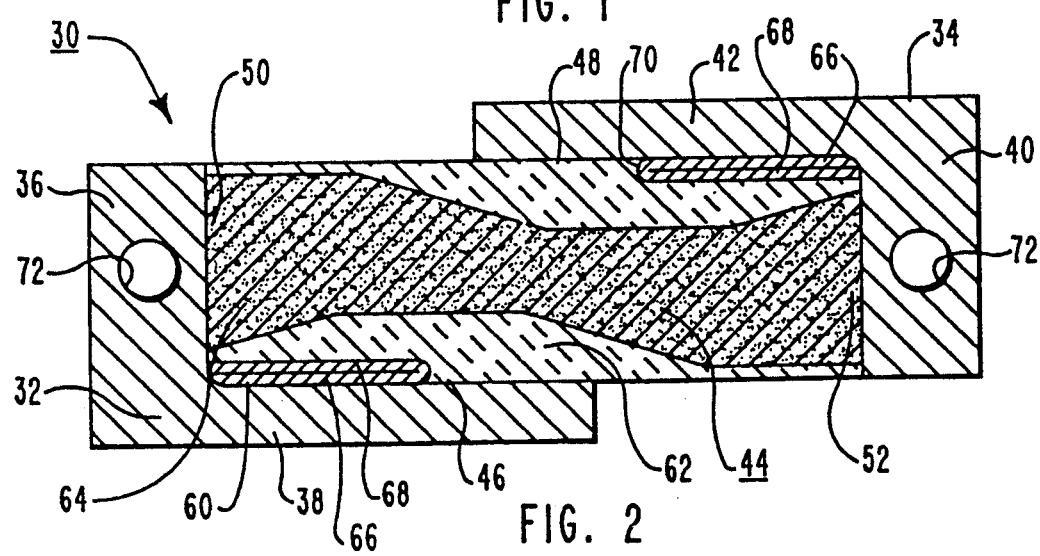
FIG. 2 is a plan view of one embodiment of the apparatus of the present invention.

With reference now to FIG. 2, one embodiment of the antisymmetric support of the present invention is illustrated at 30. The antisymmetric support 30 includes a first L-shaped test fixture 32 and a second L-shaped test fixture 34. The first L-shaped test fixture 32 includes an end segment 36 and a side segment 38. Likewise, the second L-shaped test fixture 34 includes an end segment 40 and a side segment 42.

The first L-shaped test fixture 32 and the second L-shaped test fixture 34 are antisymmetrically disposed about a test specimen 44. The test specimen 44 is attached to the antisymmetric support 30 by attaching a side 46 of the test specimen to the side 38 of the first L-shaped test fixture 32. Also, the side 48 of the test specimen is attached to the side 42 of the second L-shaped test fixture 34. The test specimen 44 is preferably disposed between the test fixtures 32 and 34 such that an end segment 50 of the test specimen 44 is disposed adjacent the end 36 of the first L-shaped test fixture 32 and an end 52 is disposed adjacent the end 40 of the second L-shaped test fixture 34.

In a presently preferred embodiment of the invention, the side segments 38 and 42 of the test fixtures are approximately the same size, as are the end segments 36 and 40. This ensures that the forces applied to the test specimen 44 through the test fixtures 32 and 34 apply to each side of the test specimen with equal magnitude.

As used herein, the term "antisymmetric" indicates a correspondence of size, shape and relative position with respect to two parts such that lines connecting corresponding points on the two parts intersect at substantially a single point or axis. Thus, if by rotating one part 180 degrees about said single point or axis of intersection it becomes aligned with its corresponding part, the two parts are said to be antisymmetrically disposed.

The first and second L-shaped test fixtures 32 and 34 may be made of a variety of materials, including steel or composite materials such as fiber reinforced plastics. The test fixtures are preferably made to simulate the rocket casing or other layer to which the grain support is attached or bonded. Thus, if it is desired to test a grain support system which is to be bonded directly to a steel rocket case, the L-shaped test fixtures are preferably made of the same steel as the subject rocket case. Thus, it is possible to simulate conditions which would exist in a solid rocket motor fit with the grain support system to be tested.

The test specimen 44 may be configured in a variety of configurations. Illustrated in FIG. 2 is a test specimen 44 designed to duplicate the grain support system 16 of the solid rocket motor 10 of FIG. 1. Thus, in accordance with the teachings of the present invention, the test specimen 44 is configured to be antisymmetric. Thus, two grain support systems are disposed in antisymmetric configuration to comprise the test specimen 44.

In the embodiment illustrated in FIG. 2, the grain support system includes a stress-relief flap 60, a layer of insulation 62 and a layer of propellant grain 64. The stress-relief flap 60 includes a first leg 66 and a second leg 68 which are hingedly connected together at hinge 70. First leg 66 is attached to the layer of insulation 62 and the second leg 68 is attached to the side segments 38 and 42 of the first and second L-shaped test fixtures 32 and 34.

While the test specimen 44 of FIG. 2 corresponds to the grain support system 16 utilized in the solid rocket motor 10 of FIG. 1, it will be appreciated that a number of grain support systems may be tested by building a corresponding test specimen 44 in accordance with the teachings of the present invention.

The L-shaped test fixtures 32 and 34 each include a mounting mechanism or other means for attachment to a tensile testing machine. As illustrated in FIG. 2, the means for attachment to the testing machine includes pin joints 72. Pin joints 72 are oppositely disposed such that uniaxial tension is applied to the L-shaped test fixtures 32 and 34, thereby uniformly applying the load across the test specimen 44.

A typical stress-relief flap 60 is made of woven Kevlar fabric. Thus, a variety of stress-relief flaps designed with the warp oriented in different directions could be tested to determine an optimal configuration. Other materials such as polyisoprene or other moldable reinforcements could also be used in constructing the stress-relief flap 60.

Depending on the size and performance requirements of the solid rocket motor, the stress-relief flap employed may be fairly small—less than 15 or 16 inches in diameter. On smaller flaps, it may be preferable to construct a test specimen 44 utilizing a stress-relief flap 60 having the actual size of that to be employed in the solid rocket motor. Of course, many applications, such as the space shuttle, require stress-relief flaps which are too large to be tested in actual size. In such situations, scaled-down versions of the stress-relief flap may be simulated in the test specimen.

Figure 3:
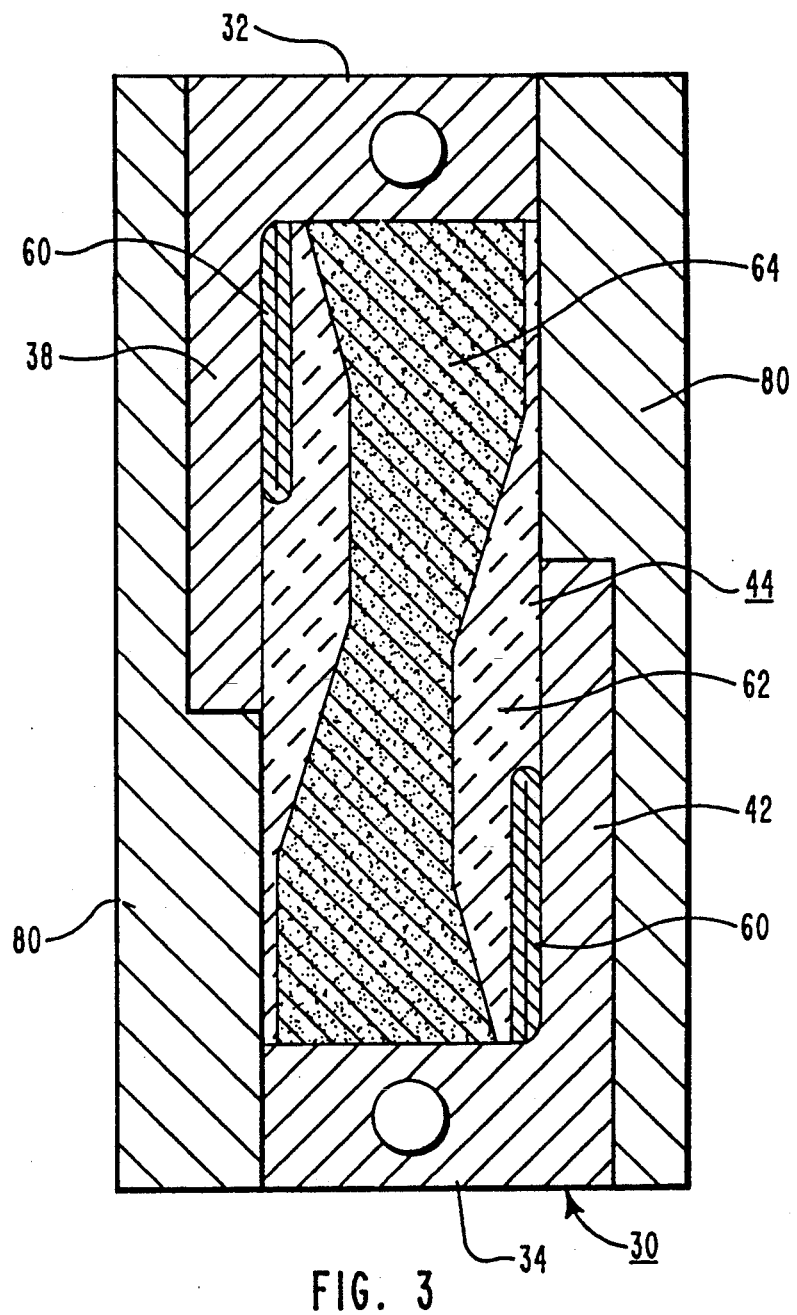
FIG. 3 is a plan view of the apparatus of FIG. 2 during the preparation of the test device.

With reference to FIG. 3, the preparation of a test specimen 44 within the antisymmetric support 30 is illustrated. A mold 80 is provided within which the L-shaped test fixtures 32 and 34 are placed in antisymmetric disposition with respect to each other. The grain support system desired to be tested is then simulated by preparing, within the mold 80, the antisymmetric support 30 in the same manner that it would in constructing a solid rocket motor.

Initially, the stress-relief flaps 60 are antisymmetrically disposed against the L-shaped fixtures 32 and 34. The antisymmetric nature of the testing device prevents the action of one grain reinforcing system from affecting the action of the other. Thus, as the device is placed under a load, the reactions of the two grain support systems are independent, enabling two sets of data to be collected for each test conducted.

The desired thickness of insulation 62 is placed against the stress-relief flaps and along the portions of the sides 38 and 42 of the L-shaped fixtures 32 and 34 which remain exposed. The insulation is also antisymmetrically disposed with-in the mold 80. Bonding between the L-shaped fixtures, the stress-relief flaps and the insulation occurs through vulcanization. The stress-relief flaps 60 and the insulation 62 are laid up in their respective positions in a "green" state. The temperature is then raised, causing the material to bond as it cures.

Following the vulcanization of the stress-relief flaps 60 and the insulation 62, propellant 64 is cast onto the insulation 62 thereby filling the void between the layers of insulation 62. So configured, the test specimen 44 simulates the cross-sectional configuration of two grain support systems antisymmetrically disposed with respect to each other. Hence, there exists a correspondence of size, shape and relative position with respect to each portion of the two simulated grain support systems such that lines connecting corresponding points on the two simulated support systems intersect at substantially a single point, substantially in the center of the support 30. By rotating one part 180 degrees about the center of the support 30, it becomes aligned with its corresponding part. The mold 80 may then be removed and the test specimen 44 is ready to be tested in a tensile testing machine.

Figure 4:
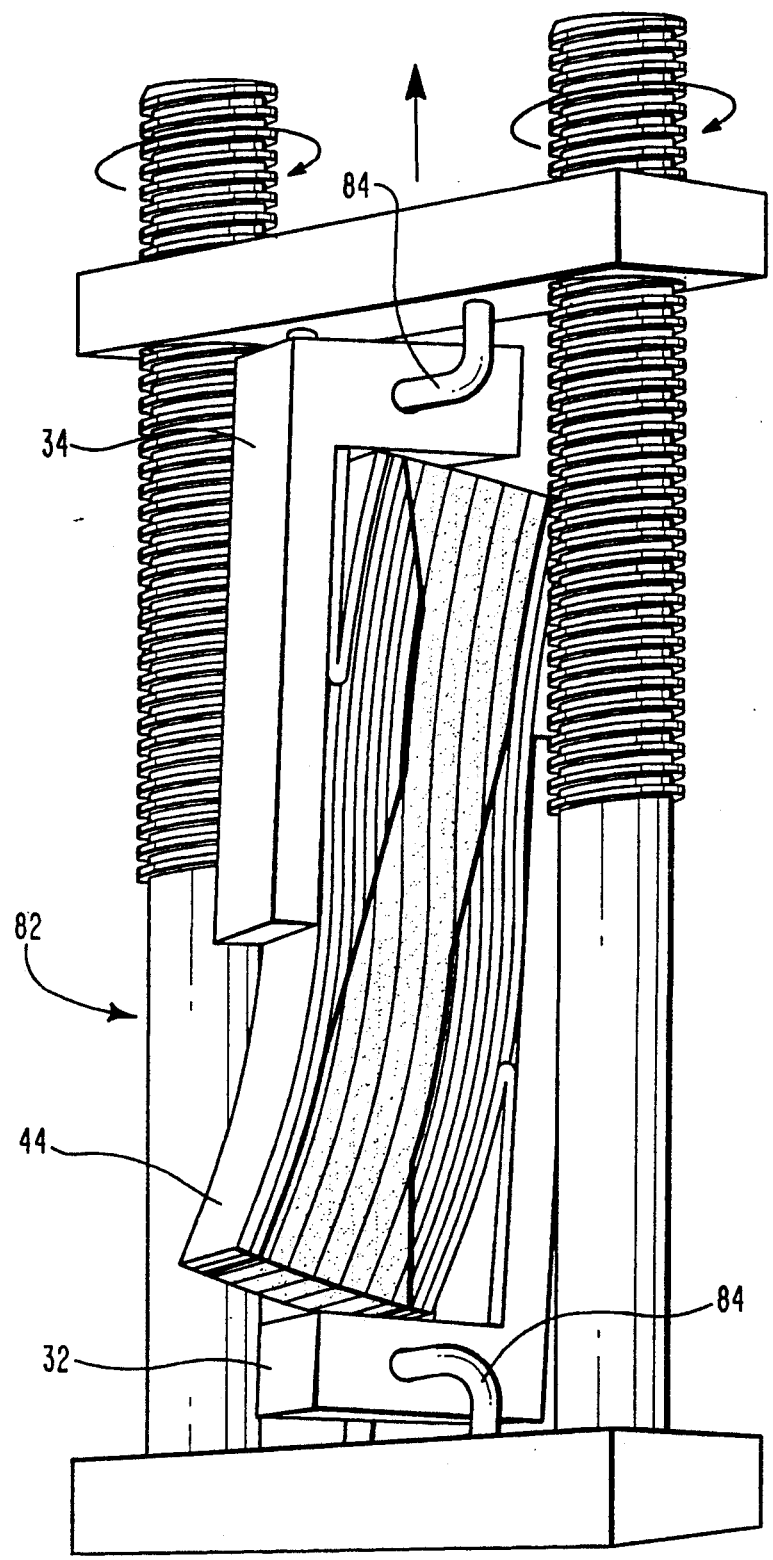
FIG. 4 is a perspective view of the apparatus of FIG. 2 during testing.

Testing of the test specimen 44 is accomplished by connecting the L-shaped test fixtures 32 and 34 to a tensile testing machine 82, such as is illustrated in FIG. 4. The tensile testing machine 82 may be any of those conventionally known for use in the art of materials testing, such as an Instron tensile testing machine.

The L-shaped test fixtures 32 and 34 are attached to the testing machine by positioning pins 84 within the pin joints 72 located at the ends of the test fixtures 32 and 34. The test specimen 44 may then be tested by following those testing procedures commonly known in the art of materials testing, such as by measuring deflection or deformation for a given load and measuring load to failure. Advantageously, the specimen 44 may be monitored visually during the testing, thereby enabling initial failure locations to be identified.

As can be observed from the foregoing, the present invention provides apparatus and methods for testing propellant grain support systems which can be effectively utilized to test materials and bonding methods about which physical properties may not be known. The invention also permits physical tests of propellant grain support systems to be conducted without the extreme cost attendant in preparing a solid rocket motor according to the experimental design and test firing the motor.

Additionally, the present invention provides an apparatus and method for testing propellant grain support systems whereby bonds and bond reinforcement systems, such as stress-relief flaps, can be visually monitored during the test, thereby obtaining specific data on the location of debonding and weaknesses in the grain support system.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for evaluating the effects of uniaxial tension to the midline of a test specimen, comprising:
   an antisymmetric test specimen having first and second opposing sides and first and second opposing ends;
   a first L-shaped test fixture including an end segment and a side segment, the side segment attached to the first side of the test specimen, said attachment of the first test fixture to the test specimen being the sole means of transferring a load from the first test fixture to the test specimen, the end segment of the first test fixture further including a first rotatable mounting mechanism for mounting the first test fixture in a tensile testing machine, the rotatable mounting mechanism configured to permit rotation of the first text fixture as a load is applied to the test specimen; and
   a second L-shaped test fixture including an end segment and a side segment, the side segment attached to the second side of the test specimen, said attachment of the second test fixture to the test specimen being the sole means of transferring a load from the second test fixture to the test specimen, the end segment of the second test fixture further including a rotatable mounting mechanism for mounting the second test fixture in a tensile testing machine, the rotatable mounting mechanism configured to permit rotation of the second test fixture as a load is applied to the test specimen.

2. An apparatus as defined in claim 1, wherein the side segments of the first and second L-shaped test fixtures are bonded to the sides of the test specimen.

3. An apparatus as defined in claim 2, wherein at least a portion of sides of the test specimen which are bonded to the test fixtures are made of insulation which is bonded to the side segments of the first and second L-shaped test fixtures through vulcanization.

4. An apparatus as defined in claim 1, wherein the first and second L-shaped test fixtures are made of steel.

5. An apparatus as defined in claim 1, wherein the first and second L-shaped test fixtures are made of a composite material.

6. An apparatus as defined in claim 1, wherein the antisymmetric test specimen includes a flap hinge on each of its sides, each flap hinge having a first and second legs hingedly connected together, the flap hinges disposed with respect to each other in antisymmetric configuration about the test specimen.

7. An apparatus as defined in claim 6, wherein the test specimen includes a layer of insulation along its first and second sides.

8. An apparatus as defined in claim 7, wherein one of the legs of each flap hinge is attached to the layer of insulation and the other leg of each flap hinge is attached to the side segments of the first and second L-shaped test fixtures.

9. A testing apparatus for use in a tensile testing machine for simulating thermal, acceleration, and ignition pressurization loads upon a grain support system of a solid rocket motor during ignition, comprising:

an antisymmetric test specimen having first and second opposing sides and first and second opposing ends and including flap hinges antisymmetrically disposed on the first and second sides of the specimen;

a first L-shaped test fixture including an end segment and a side segment, the side segment bonded to the first side of the test specimen and to the flap hinge disposed on the first side of the test specimen, said attachment of the first test fixture to the test specimen being the sole means of transferring a load from the first test fixture to the test specimen, the end segment of the first test fixture further including a first rotatable mounting mechanism for mounting the first test fixture in a tensile testing machine, the rotatable mounting mechanism configured to permit rotation of the first test fixture as a load is applied to the test specimen; and a second L-shaped test fixture including an end segment and a side segment, the side segment bonded to the second side of the test specimen and to the flap hinge disposed on the second side of the test specimen, said attachment of the second test fixture to the test specimen being the sole means of transferring a load from the second test fixture to the test specimen, the end segment of the second test fixture further including a rotatable mounting mechanism for mounting the second test fixture in a tensile testing machine, the rotatable mounting mechanism configured to permit rotation of the second test fixture as a load is applied to the test specimen, thereby permitting the application of uniaxial tension to the midline of the test specimen.

10. A test apparatus as defined in claim 9, wherein the antisymmetric test specimen includes a layer of propellant.

11. A testing apparatus as defined in claim 10, wherein the antisymmetric test specimen further includes a layer of insulation bonded about the layer of propellant.

12. A testing apparatus as defined in claim 11, wherein the layers of insulation are attached through vulcanization to at least a portion of the side segments of the first and second L-shaped test fixtures.

13. A testing apparatus as defined in claim 12, wherein one of the legs of each flap hinge is attached to the layer of insulation and the other leg of each flap hinge is attached to the side segments of the first and second L-shaped test fixtures.

14. A testing apparatus as defined in claim 13, wherein the first and second L-shaped test fixtures are made of steel.

15. A testing apparatus as defined in claim 13, wherein the first and second L-shaped test fixtures are made of a composite material.

16. A process for simulating thermal, acceleration, and ignition pressurization loads upon the grain support system of a solid rocket motor during ignition, comprising the steps of:

preparing an antisymmetric test specimen in which the grain support system of the solid rocket motor is reproduced along each side of the specimen such that the reproduced grain support systems are antisymmetrically disposed with respect to each other;

attaching a side segment of an L-shaped test fixture to each side of the test specimen, each L-shaped test fixture including an end segment configured with a rotatable mounting mechanism for mounting the test fixture in a tensile testing machine, each rotatable mounting mechanism configured to permit rotation of the test fixture to which it is mounted as a load is applied to the test specimen, said attachment of the test fixtures to the test specimen being the sole means of transferring a load from the test fixtures to the test specimen;

connecting the L-shaped test fixtures to a tensile testing machine at the rotatable mounting mechanisms; and applying tension to the test specimen.

17. A process for simulating thermal, acceleration, and ignition pressurization loads upon the grain support system of a solid rocket motor during ignition as set forth in claim 16, wherein the steps of preparing an antisymmetric test specimen and attaching a side segment of an L-shaped test fixture to each side of the test specimen further include the steps of bonding one side of a flap hinge to each side segment of the test fixtures, bonding a layer of insulation over the opposite side of each flap hinge and onto any exposed portions of the side segments of the test fixtures such that the resulting combination of flap hinge and insulation layer reproduces the grain support system of the solid rocket motor, disposing the test fixtures such that they have an antisymmetric orientation with respect to each other; and casting propellant between the layers of insulation such that the reproduced grain support systems are bonded to each other in antisymmetric disposition.

18. A process for simulating thermal, acceleration, and ignition pressurization loads upon the grain support system of a solid rocket motor during ignition as set forth in claim 17, wherein the steps of preparing an antisymmetric test specimen and attaching a side segment of an L-shaped test fixture to each side of the test specimen are accomplished after positioning the test fixtures against a mold thereby disposing the test fixtures with an antisymmetric orientation with respect to each other.

19. An apparatus for evaluating the effects of uniaxial tension to the midline of a test specimen, comprising:

an antisymmetric test specimen having first and second opposing sides and first and second opposing ends;

a first L-shaped test fixture including an end segment and a side segment, the side segment capable of attachment to the first side of the test specimen such that the end segment is disposed adjacent the first end of the test specimen; and a second L-shaped test fixture including an end segment and a side segment, the side segment capable of attachment to the second side of the test specimen such that the end segment is disposed adjacent the second end of the test specimen;

wherein the side segments of the first and second L-shaped test fixtures are bonded to the sides of the test specimen and at least a portion of sides of the test specimen which are mounted to the test fixtures are made of insulation which is bonded to the side segments of the first and second L-shaped test fixtures through vulcanization.

* * * * *